(12) United States Patent
White

(10) Patent No.: US 7,850,595 B2
(45) Date of Patent: Dec. 14, 2010

(54) TRANSFERRING AND HOLDING DEVICE FOR HIGH-RISK NEONATAL INTENSIVE CARE UNIT (NICU) PATIENTS

(76) Inventor: Robert D. White, 1900 Briar Rd., Niles, MI (US) 49120

( * ) Notice: Subject to any disclaimer, the term of this patent is extended or adjusted under 35 U.S.C. 154(b) by 719 days.

(21) Appl. No.: 11/650,769

(22) Filed: Jan. 8, 2007

(65) Prior Publication Data

US 2008/0163425 A1  Jul. 10, 2008

(51) Int. Cl.
*A61G 11/00* (2006.01)

(52) U.S. Cl. ............................................. 600/22

(58) Field of Classification Search ............ 600/21–22; 128/845, 897; 5/1, 600, 603, 607–624
See application file for complete search history.

(56) References Cited

U.S. PATENT DOCUMENTS

| | | | |
|---|---|---|---|
| 3,813,712 A * | 6/1974 | Bonnin | 5/625 |
| 4,712,258 A * | 12/1987 | Eves | 5/424 |
| 4,795,429 A | 1/1989 | Feldstein | |
| 4,802,244 A | 2/1989 | McGrath-Saleh | |
| 4,971,271 A | 11/1990 | Sularz | |
| 4,988,062 A | 1/1991 | London | |
| 5,056,533 A | 10/1991 | Solano | |
| 5,226,892 A | 7/1993 | Boswell | |
| 5,261,133 A | 11/1993 | Wilkerson | |
| 5,263,941 A | 11/1993 | Cockrill | |
| 5,334,186 A | 8/1994 | Alexander | |
| 5,387,177 A | 2/1995 | Dunn | |
| 5,427,338 A | 6/1995 | Garrett et al. | |
| D378,408 S | 3/1997 | Pyeatt et al. | |
| D379,509 S | 5/1997 | Macko | |
| 5,855,031 A * | 1/1999 | Swift, Jr. | 5/93.1 |
| 6,367,476 B1 | 4/2002 | Conn | |
| 6,382,568 B1 | 5/2002 | Snell | |
| 6,458,104 B2 | 10/2002 | Gautsche | |
| 6,615,426 B1 * | 9/2003 | Risk, Jr. | 5/425 |
| 7,246,388 B2 * | 7/2007 | DiLiberto, Jr. | 5/425 |
| 2004/0236174 A1 | 11/2004 | Boone et al. | |
| 2005/0103949 A1 | 5/2005 | Ross et al. | |
| 2006/0206978 A1 | 9/2006 | Hilton et al. | |

OTHER PUBLICATIONS

International Search Report issued in corresponding International Application, mailed Aug. 20, 2008, 2 pages.

* cited by examiner

*Primary Examiner*—John P Lacyk
(74) *Attorney, Agent, or Firm*—Baker & Daniels LLP

(57) ABSTRACT

A transferring and holding device and method for holding infants having lifelines, such as IV tubes, monitor wire leads, and ventilator tubes, connected thereto. In one embodiment, the device includes a support surface adapted to hold an infant; a boundary attached to and bolstering the support surface; and at least one securing mechanism adapted to secure the lifelines and to impede the lifelines from being disconnected from the infant. The support surface preferably has openings to enable skin-to-skin contact between the infant and a person holding the infant, and at least a portion of the support surface can be a nonabsorbent, open-weave webbed material. The boundary may include a foam member, and/or a flexible plastic or metal member to provide structural support.

37 Claims, 11 Drawing Sheets

TRANSFERRING AND HOLDING DEVICE FOR HIGH-RISK NEONATAL INTENSIVE CARE UNIT (NICU) PATIENTS

BACKGROUND OF THE INVENTION

This invention relates to a transferring and holding device for high-risk neonatal intensive care unit (NICU) patients, and in particular, to a transferring and holding device including a securing mechanism to secure lifelines, such as IV tubes, monitoring lead wires, and/or ventilator tubes, that are connected to an NICU patient.

It is known that holding an infant benefits both the infant and the parents by providing security and bonding. However, for a high-risk neonatal intensive care unit (NICU) infant, this seemingly simple task can be a very complicated matter. A critically ill infant may have a dozen or more tubes and wires connecting him or her to life-support and monitoring equipment. The NICU infant may be stable enough to be held by and benefit from human contact; however, such contact can pose a significant risk of dislodging one or more of the lifelines in the process of transferring the infant from the bed into the parents' arms and back again. This can make the experience of holding an NICU infant considerably more stressful for both the parents and NICU staff.

U.S. Pat. No. 5,387,177 (the '177 patent) to Dunn discloses an adjustable pediatric incubator nest. The incubator nest includes a resilient base member and adjustable resilient foam sides. A fabric material is provided on the resilient base member, and the sides include a plurality of slits and selectively removable segments for holding tubes. The length and width of the base member is preferably made to match a specific incubator in which the nest is to be used. The '177 patent does not address how to move an infant who has lifelines attached.

U.S. Pat. No. 4,802,244 to McGrath-Saleh discloses a premature infant bedding construction. The bedding includes a generally U-shaped retaining wall that is constructed of a polyester fiber-filled tube. The tube is formed from sewn lambskin. A lambskin base pad is attached to the bottom of the retaining wall for supporting an infant. The bedding construction also includes a harness to hold the infant; however, the bedding construction does not include any mechanism to secure lifelines connected to the infant.

U.S. Patent Application Publication 2006/0206978 A1 to Hilton et al. discloses a vest for holding an NICU infant. The vest includes a plurality of relocatable straps containing hook material on one side for attaching to loop material on the exterior of the vest so that the straps may be located where desired to hold IV tubes or other medical tubing. No mechanism is provided for holding the tubes when transferring the infant from a bed to the vest.

SUMMARY OF THE INVENTION

In one embodiment of the invention, a transferring and holding device is provided for infants having lifelines, such as IV tubes, monitor wire leads, and ventilator tubes, connected thereto. The device includes a support surface adapted to hold an infant; a generally U-shaped boundary attached to and bolstering the support surface; and at least one securing mechanism adapted to secure the lifelines and to impede the lifelines from being disconnected from the infant.

The support surface may have openings to enable skin-to-skin contact between the infant and a person holding the infant. At least a portion of the support surface may be a nonabsorbent, open-weave webbed material.

The boundary may include a foam member, and/or may include a flexible plastic or metal member to provide structural support. The boundary can be removable for separate washing of or replacement of the support surface. The support surface may include sleeves for insertion of at least a portion of the boundary to facilitate removable attachment thereof.

In one embodiment, the transferring and holding device includes at least two securing mechanisms, wherein one of the securing mechanisms is located on the device in an area that is above a region on the support surface configured to hold the head of the infant.

The securing mechanism may also include a base and spaced-apart pegs extending from the base. Some of the lifelines fit between the pegs and others are wrapped around the pegs for securing the lifeline to the securing mechanism. The device may further include a cap, and wherein the securing mechanism is configured for lifelines to be positioned between the base and the cap. The cap may include openings configured and spaced apart to receive corresponding pegs, and the securing mechanism may further include a securing device to secure the cap to the base.

In another embodiment, the securing mechanism has a base having slots for receipt of the lifelines and collars that are attachable to the lifelines to limit the movement of the lifelines with respect to the boundary. The securing mechanism may further include a cap covering the slots in the base.

In still another embodiment, the securing mechanism includes hooks and rings. One of either the hooks or rings are attachable to respective lifelines and the other are attached to the boundary. The hooks may include a releasable clasp.

In another embodiment of the invention, a transferring and holding device is provided for infants having lifelines, such as IV tubes, monitor wire leads, and ventilator tubes, connected thereto, wherein the transferring and holding device includes a support surface adapted to hold an infant; and at least one securing mechanism adapted to secure the lifelines and to impede the lifelines from being disconnected from the infant, and wherein at least a portion of the securing mechanism is attached to the device and located in an area that extends above a region on the support surface configured to hold the head of the infant.

The securing mechanism may be removable and relocatable on the securing mechanism. The support surface may include openings to enable skin-to-skin contact between the infant and a person holding the infant.

The device may further include a boundary attached to and bolstering the support surface. The boundary can have a generally U-shaped configuration with the base of the U extending above the region of the support surface configured to hold the head of the infant. The boundary may include a foam member, and/or a plastic or metallic member that adds structural support to the device.

The securing mechanism may include a base and pegs extending from and spaced apart on the base, and some lifelines may extend between the pegs, and others can be wrapped around the pegs to limit movement of the lifelines relative to the securing mechanism. Alternately, the securing mechanism may have a base with slots to receive lifelines and collars attachable to the lifelines to limit movement of the lifelines with respect to the infant. In another embodiment, the securing mechanism includes hooks and rings, and one of either the hooks or rings are attachable to respective lifelines and the other are attached to the device.

It is also an embodiment of the invention to provide a method for transferring and holding an infant having lifelines, such as IV tubes, monitor wire leads, and ventilator tubes, connected between the infant and medical equipment so as to impede the lifelines from being disconnected from the infant when transferring the infant from a bed into the arms of a person holding the infant, wherein the method includes the steps of providing a transferring and holding device having a support surface configured to hold an infant and at least one securing mechanism to secure lifelines connected to the infant; placing the infant on the support surface; securing the lifelines to the securing mechanism before moving the infant; and transferring the infant, from a bed into the arms of a person to hold the infant using the transferring and holding device.

The method may further include the step of providing openings in the support surface to enable skin-to-skin contact between the infant and the person holding the infant. The method may also include the step of providing a boundary on the transferring and holding device that bolsters the support surface. The boundary can have a generally U-shaped configuration with the bottom of the U extending over the infant's head. The boundary may include a flexible plastic or metallic member to provide structural support to the device and securing mechanism.

The method for transferring and holding an infant having lifelines may also include the step of having at least a portion of the securing mechanism located over the top of the head of the infant. The securing mechanism may include a base and pegs that are spaced apart on and extending from the base. The method may further include the step of wrapping at least one of the lifelines around the pegs to secure the lifeline thereto. Alternately, the securing mechanism may have a base having slots configured to receive respective lifelines and collars that are attachable to the lifelines. The method may further include the step of attaching collars to respective lifelines to limit the movement of the lifelines relative to the securing mechanism. In another embodiment, the securing mechanism may include hooks and rings, and the method for holding an infant may further include the steps of attaching one of either the hooks or rings to the transferring and holding device and the other to respective lifelines and securing the hooks to respective rings to limit movement of the lifelines with respect to the device.

In another embodiment of the invention, a securing mechanism is provided for securing lifelines, such as IV tubes, monitor lead wires, and ventilator tubes, connected to an infant, wherein the securing mechanism includes a base and pegs spaced apart on and extending from the base. At least some of the pegs are spaced apart so as to permit a ventilator tube to extend therebetween, and other pegs are adapted to have a lifeline wrapped therearound. The securing mechanism may further include a cap, and the mechanism is configured for lifelines to be positioned between the cap and the base. The cap may include openings configured and spaced apart to receive corresponding pegs on the base. The securing mechanism may further include at least one securing device to secure the cap to the base. A material may be wrapped about the pegs to increase friction between the pegs and lifelines to prevent slippage thereof.

In a different embodiment of the invention, a securing mechanism is provided for securing lifelines, such as IV tubes, monitor lead wires, and ventilator tubes, connected to an infant, wherein the securing mechanism includes a base having slots configured to receive the lifelines and collars attachable to the lifelines to limit movement of the lifelines with respect to the base. The securing mechanism may further include a cap covering the slots in the base.

In yet another embodiment of the invention, a securing mechanism is provided for securing lifelines, such as IV tubes, monitor lead wires, and ventilator tubes, connected to an infant, wherein the securing mechanism includes hooks and rings with one of either the hooks or rings attached to the securing mechanism and the other attached to respective lifelines. The hooks may include a releasable clasp.

BRIEF DESCRIPTION OF THE DRAWINGS

The above-mentioned and other features and objects of this invention and the manner of obtaining them will become more apparent, and the invention itself will be better understood by reference to the following description of embodiments of the present invention taken in conjunction with the accompanying drawings, wherein.

Figure 1:
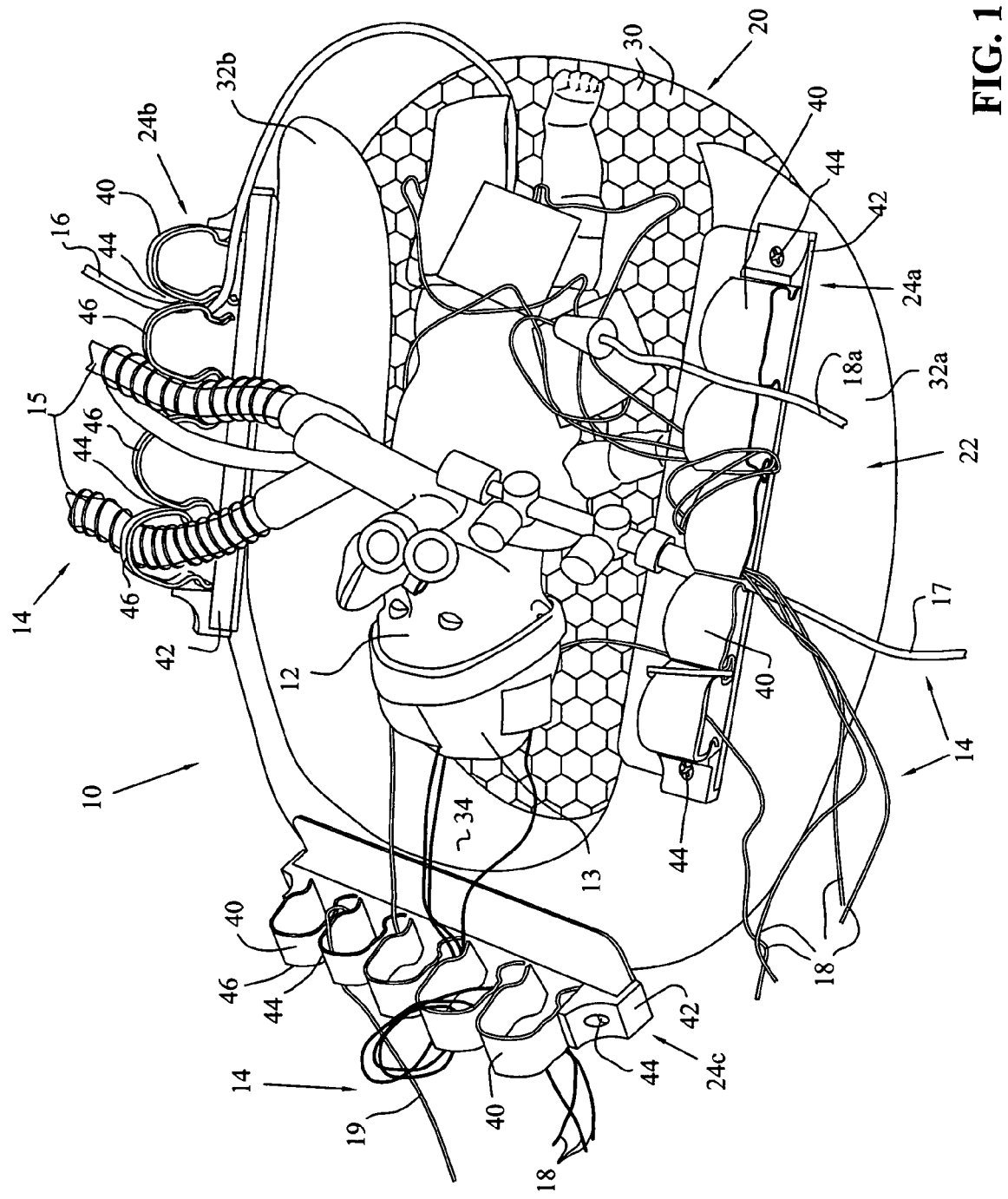
FIG. 1 is a perspective view of one embodiment of the subject invention for a transferring and holding device having securing mechanisms to secure lifelines connected to an infant.

Corresponding reference characters indicate corresponding parts throughout the several views. Although the drawings represent embodiments of the present invention, the drawings are not necessarily to scale and certain features may be exaggerated in order to better illustrate and explain the present invention. The exemplification set out herein illustrates certain embodiments of the invention, and such exemplifications are not to be construed as limiting the scope of the invention in any manner.

DETAILED DESCRIPTION OF EMBODIMENTS OF THE INVENTION

For the purposes of promoting an understanding of the principles of the invention, reference will now be made to the embodiments illustrated in the drawings, which are described below. It will nevertheless be understood that no limitation of the scope of the invention is thereby intended. The invention includes any alterations and further modifications in the illustrated devices and described methods and further applications of the principles of the invention, which would normally occur to one skilled in the art to which the invention relates.

Figure 2:
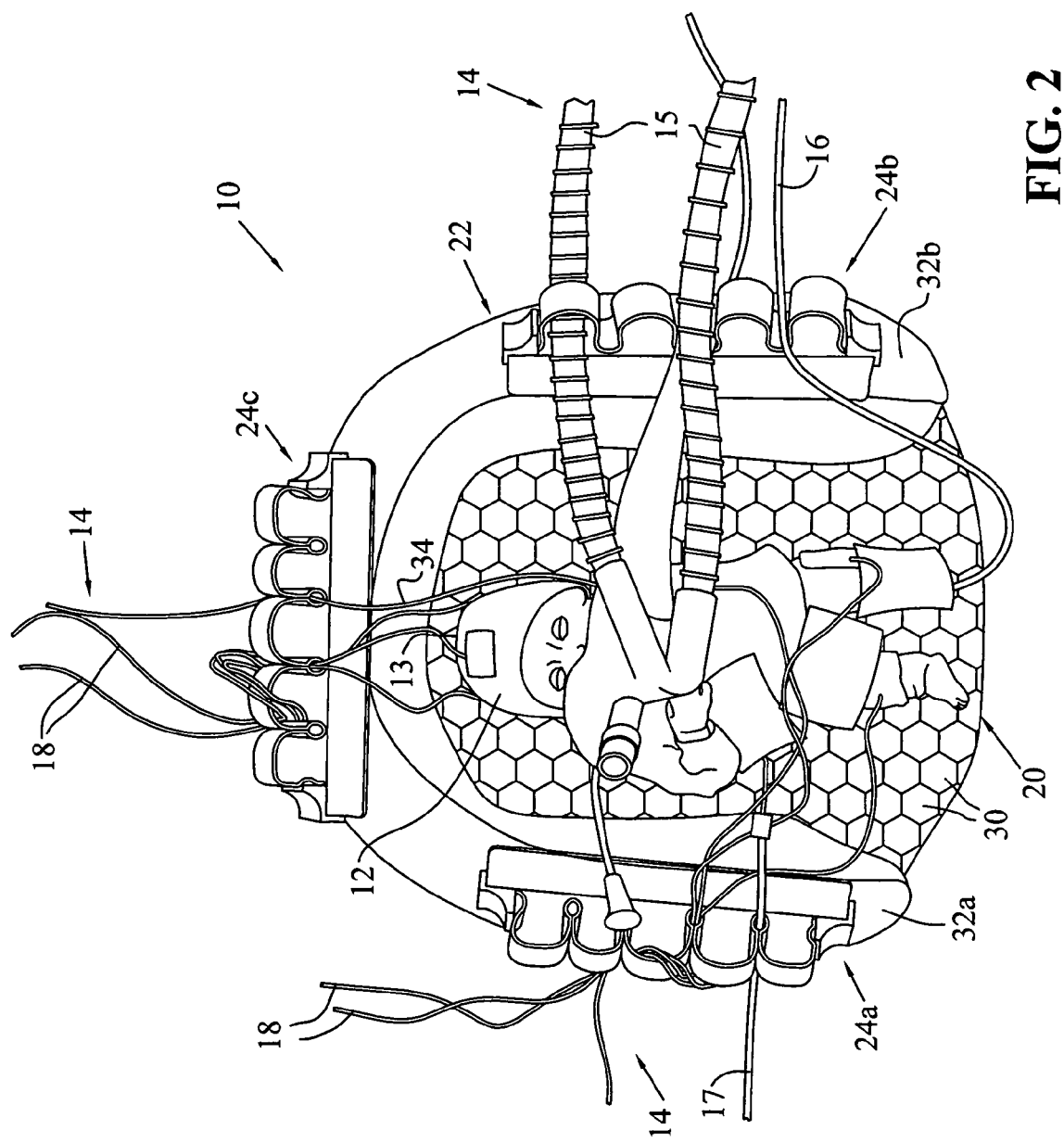
FIG. 2 is a plan view of the device of FIG. 1.

Referring to FIGS. 1 and 2, one embodiment of a transferring and holding device for an NICU or lower-acuity pediatric intensive care unit (PICU) infant is shown, generally indicated as 10. Transferring and holding device 10 is designed and configured to hold an infant 12, wherein the crown of the infant's head is designated as 13. Device 10 also secures lifelines, generally indicated as 14, which include tubes and wires attached to medical equipment for sustaining and monitoring the status of infant 12. Lifelines 14 do not form a part of the transferring and holding device and may include a variety of known lines, such as flexible ventilator tubing 15, an oximeter cable 16, an umbilical catheter 17, EKG wires 18, a temperature probe 18a, and a feeding tube 19. It should be appreciated that the type, number, and location of lifelines 14 will vary depending upon the particular condition, age, size, and ailments of infant 12.

In this embodiment, transferring and holding device 10 includes a support or sleeping surface, generally indicated as 20, which is configured to hold infant 12 in a comfortable manner; a boundary, generally indicated as 22, for providing support to the sleeping surface; and a plurality of securing mechanisms, generally indicated as 24a, 24b and 24c, designed to secure lifelines 14 and prevent the lifelines from being dislodged, crimped or disconnected from infant 12 when transporting the infant from a bed into the arms of a parent or caregiver as is discussed in further detail below.

Sleeping surface 20 preferably includes openings 30 to allow skin-to-skin contact between infant 12 and a person holding the infant. In the embodiment shown, sleeping surface 20 is made from a nonabsorbent material, such as nylon or polyester, that is provided in a weaved, web configuration.

In the embodiment of FIGS. 1 and 2, boundary 22 has a generally U-shaped configuration, including sides 32a and 32b and a base portion 34. Sides 32a and 32b extend along and straddle the sides of infant 12 while base portion 34 extends over the crown 13 of infant 12's head. As used in the specification and claims herein, when referring to the boundary or a securing mechanism being located above or over the crown of the head of the infant, this relates to the relative positioning between the crown 13 of infant 12 and base portion 34 of boundary 22 or the relative position between securing mechanism 24c and crown 13. Boundary 22 can be made from a foam material to provide soft support and may be covered with a sanitary nonabsorbent material. Boundary 22 can also include plastic or metallic inserts for additional support. Boundary 22 can be permanently attached to support surface 20 using an adhesive, stitches or straps, or the boundary may be removably attached with releasable fasteners, such as snaps or hook and loop fasteners, to permit the sleeping surface to be removed for washing or replacement.

In the embodiment shown, securing mechanisms 24a-24c each includes resilient clips 40 attached to a base 42 with fasteners 44. Clips 40 have a generally serpentine configuration with expandable gaps 44 located between humps 46. The lifelines are located in gaps 44 or in openings beneath the humps. Securing mechanisms 24a-24c may be permanently attached to the boundary using an adhesive or other known attaching techniques, or the securing mechanisms may be removably attached to the boundary with known devices, such as hook and loop fasteners or snaps. Attaching the securing mechanisms in a removable fashion offers the advantage of being able to remove one or more of the securing mechanisms that a particular infant may not need. Additionally, this allows the securing mechanisms to be repositioned to a preferred location based upon the size of the infant and particular lifelines connected thereto.

To use the device, the patient or infant is first placed on the support surface 20 as shown in FIGS. 1 and 2. Device 10 and support surface 20 are configured for the crown 13 of the head of infant 12 to be placed facing the base portion 34 of boundary 22 as shown. In this manner, securing mechanism 24c will also be located over the crown of infant 12. Larger lifelines, such as ventilator tubes 15, may be placed in the opening under humps 46 of clips 40 or between the humps in a gap 44 as shown in FIGS. 1 and 2. For wires, such as EKG wires 18, and smaller tubing, such as feeding tube 19, the lifelines may be looped through and around clips 40 in order to provide additional security to prevent the lifelines from being disconnected if they are accidentally tugged or pulled.

Although the clips are shown having a uniform configuration, it is contemplated to provide the clips with varied sizes of gaps to better match the size of the lifelines to be held. It should further be appreciated that the clips are designed and of sufficient stiffness to firmly hold the lifelines to prevent them from being disconnected from infant 12, yet not so tight so as to crimp or otherwise impair the function of the tubes or other lifelines. It should be further appreciated that materials used to make device 10 should be non-toxic and preferably recyclable. The materials should also be radiolucent, nonabsorbent, CT- and MRI-compatible. It is further contemplated that device 10 and materials thereof may be sanitized for re-use or may be designed for single-patient use.

An important benefit of the invention is that an infant may have a multiplicity of lifelines connected to life-support equipment, yet still be stable enough to be held and benefit from human contact. The subject invention provides a mechanism and method to permit an infant having such lifelines to be picked up and transferred from a bed or incubator into the arms of a parent or caregiver while preventing the lifelines from becoming disconnected or crimped. If an infant cannot be removed from device 10 because of the number of lifelines while being held by the parent, openings 30 in support surface 20 will still permit skin-to-skin contact between the infant and holder thereof through the support surface.

Figure 3:
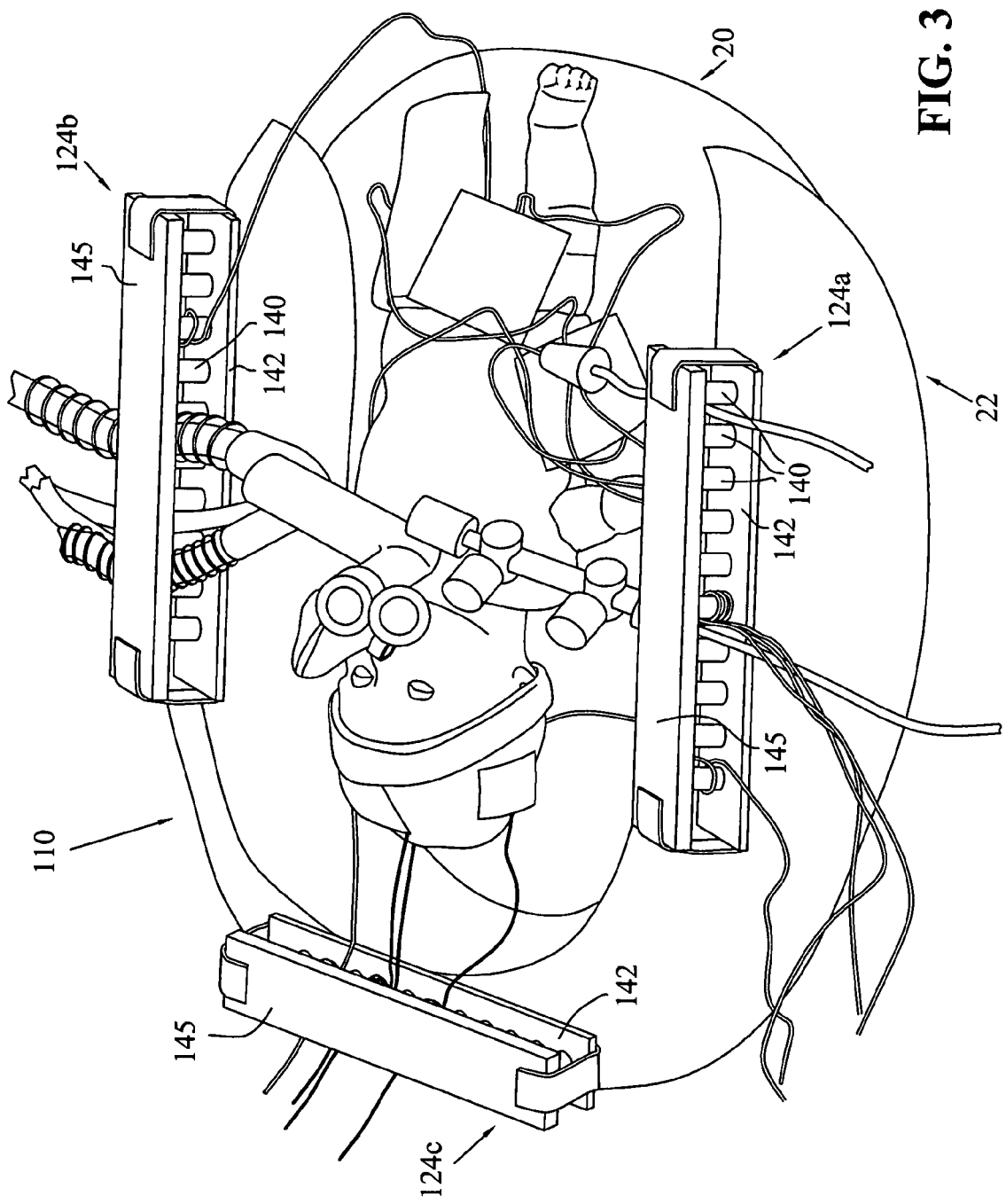
FIG. 3 is a perspective view of a transferring and holding device having alternate securing mechanisms to secure lifelines connected to an infant.
Figure 9:
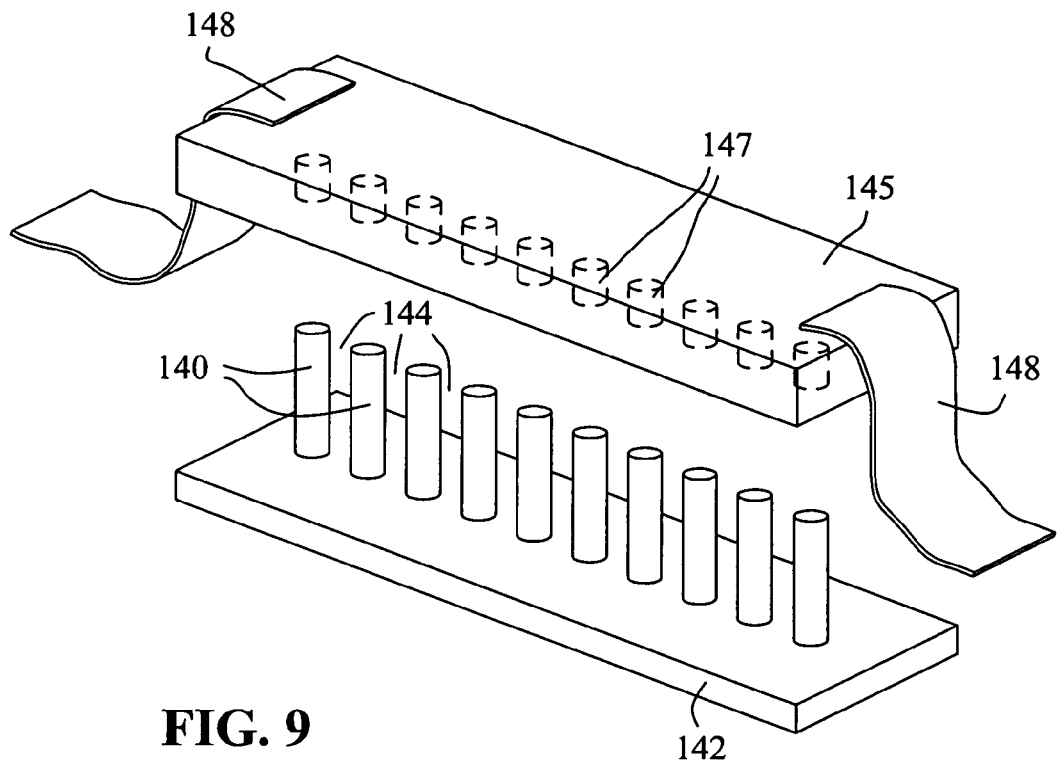
FIG. 9 is an exploded perspective view of one embodiment of a lifeline securing mechanism for use with the subject invention.
Figure 10:
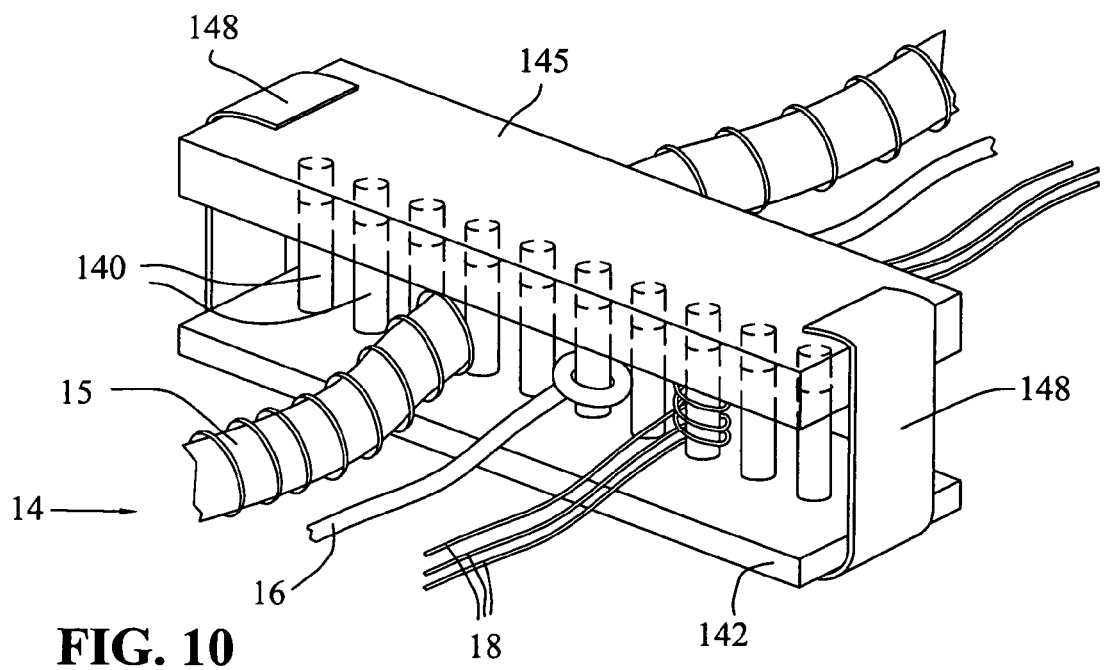
FIG. 10 is an assembled view of the lifeline securing mechanism of FIG. 9.

Now referring to FIG. 3, an alternate embodiment transferring and holding device is shown, generally indicated as 110. Device 110 is similar in other respects to transferring and holding device 10, except that it includes alternate embodiment securing mechanisms 124a, 124b and 124c. Securing mechanisms 124a-124c each include pegs 140, spaced apart and extending generally perpendicular from a base 142 as best shown in FIGS. 9 and 10. Pegs 140 define gaps 144 therebetween, which are configured to receive lifelines 14. Pegs 144 may be manufactured from or include a high friction material wrapped therearound to prevent unintended sliding of lifelines 14 in gaps 144. Securing mechanisms 124a-124c also include a cap 145 having holes or recesses 147 located in the bottom side thereof that are configured to receive pegs. Holes 147 may extend partially through or completely through cap 145. Securing mechanisms 124a-124c also include securing devices 148 for securing caps 145 to bases 142. In the embodiment shown, securing devices 148 include straps attached to cap 145, the straps having a hook material located on the underside thereof. The straps are attachable to loop material located beneath base 142 to secure cap 145 as shown in FIG. 10.

To use transferring and holding device 110, caps 145 are removed from the respective base 142, and the lifelines are placed between pegs 140 in gaps 144, as shown in FIG. 10. Smaller lifelines, such as oximeter cable 16 and EKG wires 18, may be wrapped around the respective pegs 140 to keep the lifelines from being unintentionally pulled and disconnected from infant 12. As discussed above, pegs 140 may be manufactured from or have a high-resistance material wrapped therearound to help preclude the lifelines from sliding in gaps 144 relative to pegs 140.

Figure 4:
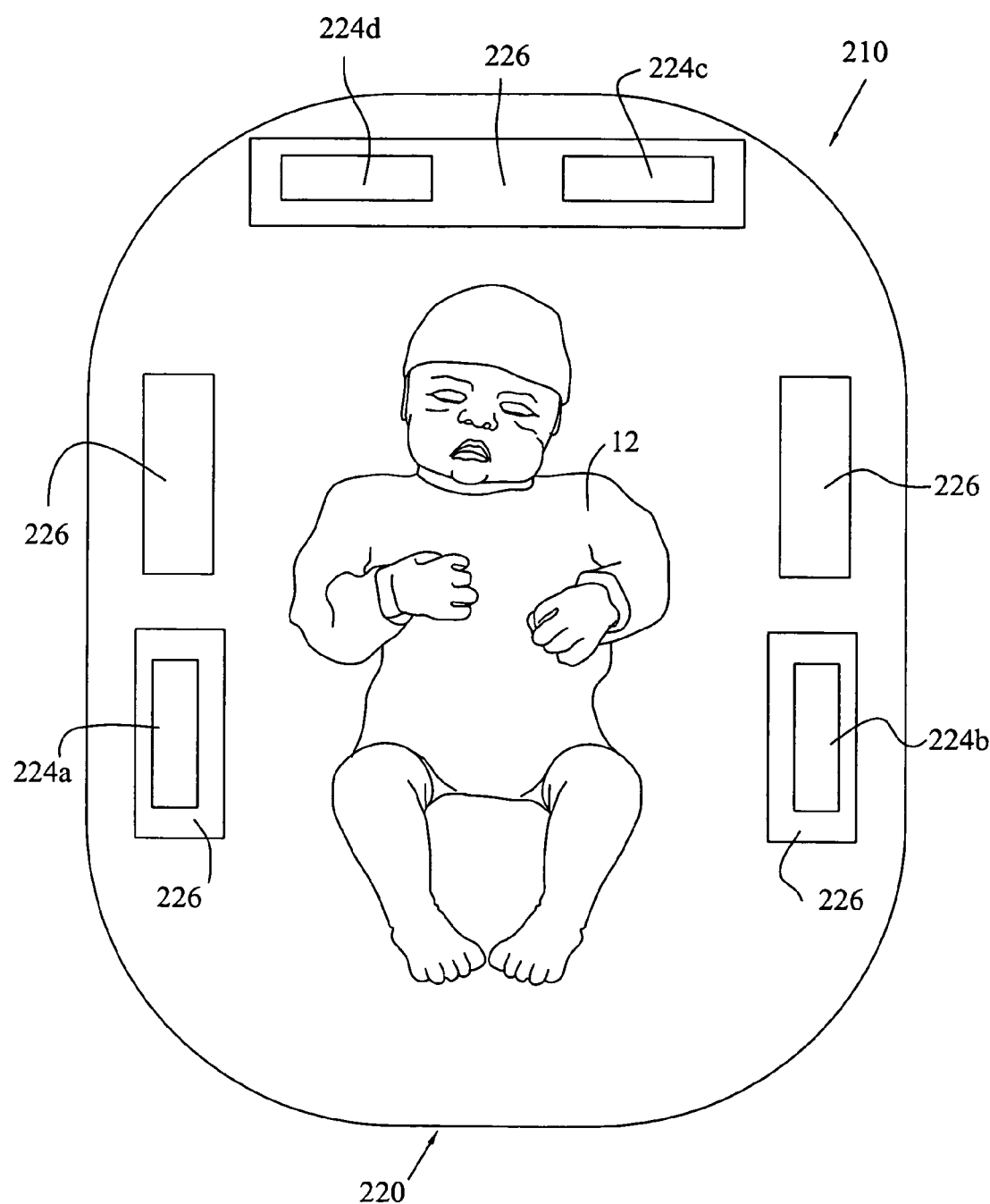
FIG. 4 is a plan view of an alternate embodiment of a transferring and holding device with relocatable securing mechanisms to secure lifelines connected to an infant.

Now referring to FIG. 4, another alternate embodiment transferring and holding device is shown, generally indicated as 210. Device 210 includes a sleeping surface 220, which can be made from material similar to that of support surface 20 discussed above. However, to increase the flexibility of the support surface, device 210 does not include a boundary. Device 210 also includes securing mechanisms 224a, 224b, 224c, and 224d that can be of the same type as either support mechanisms 24a-24c or 124a-124c discussed above or any other securing mechanisms discussed herein. In this embodiment, securing mechanisms 224a-224d are removably attached to support surface 220. Support surface 220 includes a loop material 226 placed and attached in desired locations. It should be appreciated that securing mechanisms 224a-224d are provided with a hook material, as is known, attached to the bottom thereof for removably attaching the securing mechanisms in desired locations to loop material 226. It should also be appreciated that, alternately, hook material may be provided on support surface 220 and loop material on the bottom of the securing mechanisms. As this embodiment is very flexible, it is very effective in allowing greater contact between the infant and the person holding the infant while still securing the lifelines.

Now referring to FIGS. 5-8, another alternate embodiment transferring and holding device is shown, generally indicated as 310 in which the lifelines have been removed for clarity. Device 310 includes a support surface 320 and a generally U-shaped support or boundary 322. Support surface 320 can be made from materials similar to those discussed above for the other support surfaces. Support surface 320 also includes a pair of sleeves 331 with one each on opposite sides of support surface 320 to receive respective sides of the boundary as discussed below. In the embodiment shown, sleeves 331 are open at both ends 333 and attached along both sides 335. The sleeves 331 may be attached to either the top or the bottom of support surface 320; however, in the embodiment shown, the sleeves are attached to the bottom side of support surface 320 so that boundary 322 will also be positioned beneath the support surface. Boundary 322 includes sides 337a and 337b and a base portion 339. Boundary 322 may be made from a metal or plastic material and is preferably sized in both width and thickness to provide support to device 310, yet also allow some flexibility.

Figure 5:
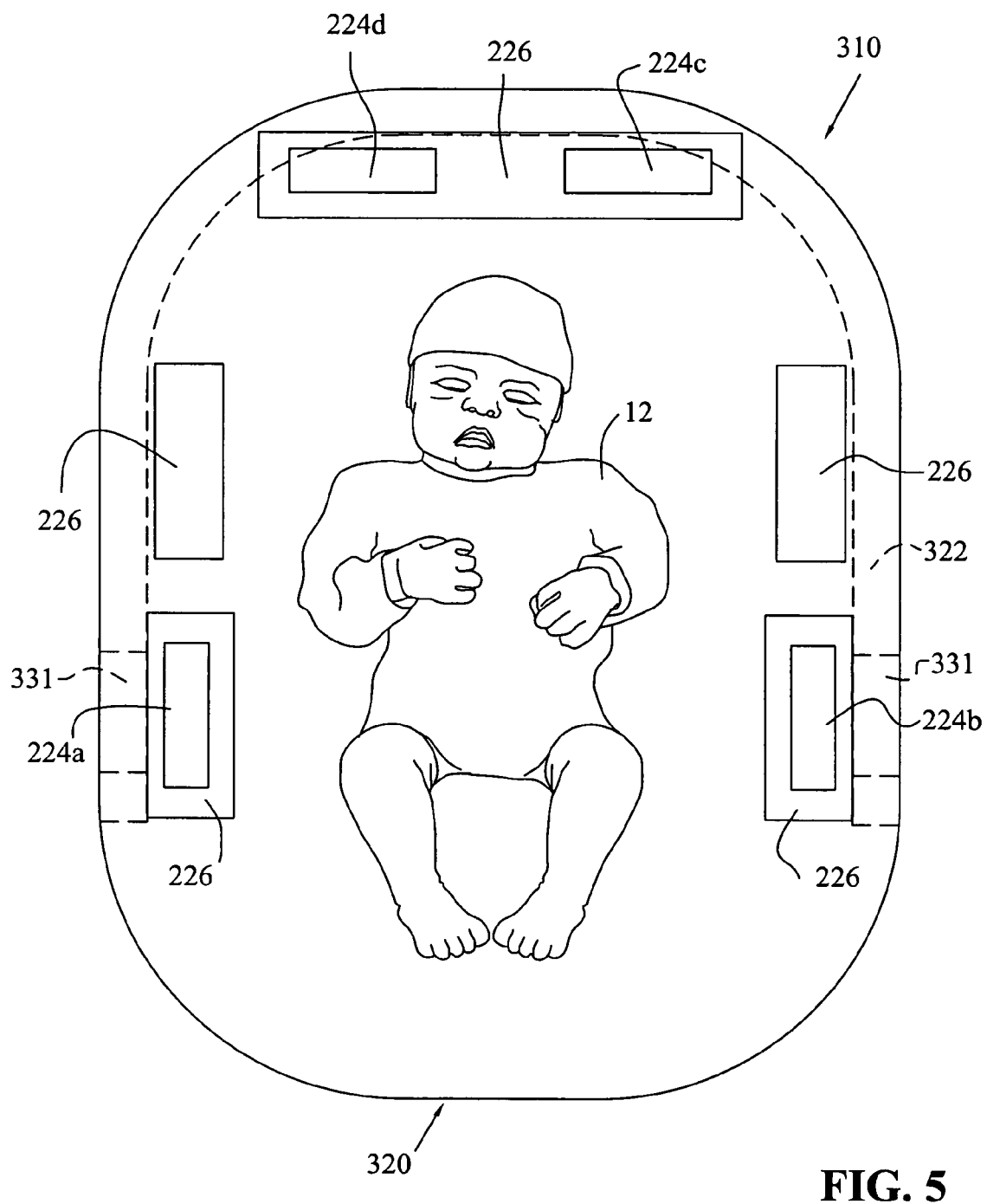
FIG. 5 is a plan view of another embodiment of a transferring and holding device with securing mechanisms to secure lifelines connected to an infant.
Figure 6:
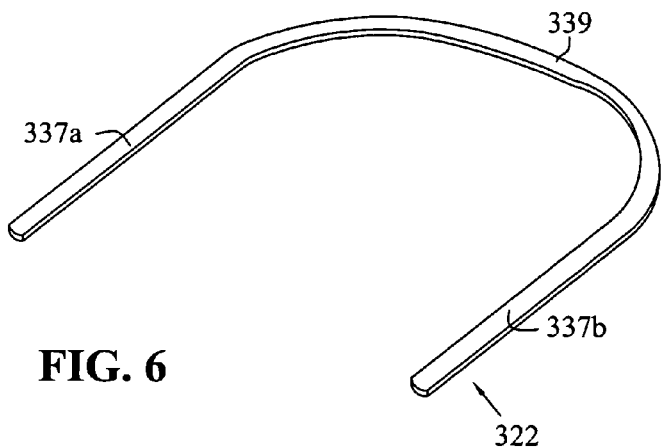
FIG. 6 is a perspective view of a U-shaped support member for the device of FIG. 5.
Figure 7:
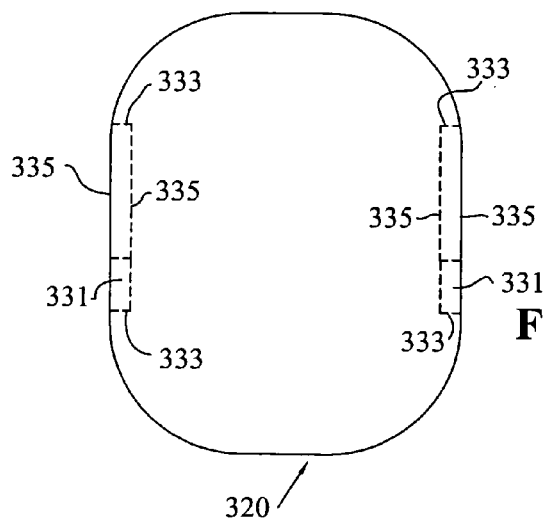
FIG. 7 is a plan view of the holding or sleeping surface of the device of FIG. 5.
Figure 8:
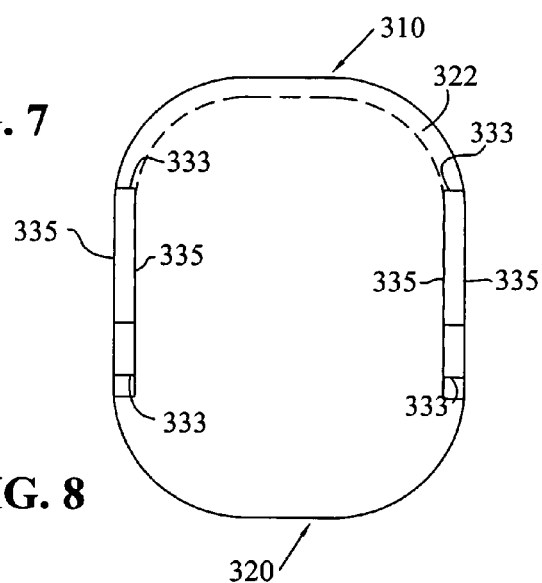
FIG. 8 is a bottom view of the device of FIG. 5 without an infant thereon and with the lifeline securing mechanisms removed.

To assemble and use device 310, the ends of sides 337a and 337b of boundary 322 are inserted through the upper opening 333 of each sleeve 331, and the sides are slid through the sleeves until boundary 322 is positioned as shown in FIG. 8. In this manner, securing devices 224a-224d can be attached where desired to loop material 226 on the top of the support surface as shown in FIG. 5. It should be appreciated that attached sides 335 of sleeves 331 may be attached to boundary 322 using known techniques, such as sewing, hook and loop fasteners, or snaps. This enables removal of boundary 322 so that support surface 320 can be washed or replaced. However, it should be realized that the sleeves 331 could extend further along support surface 320 and that boundary 322 may be permanently attached therein if desired.

Figure 11:
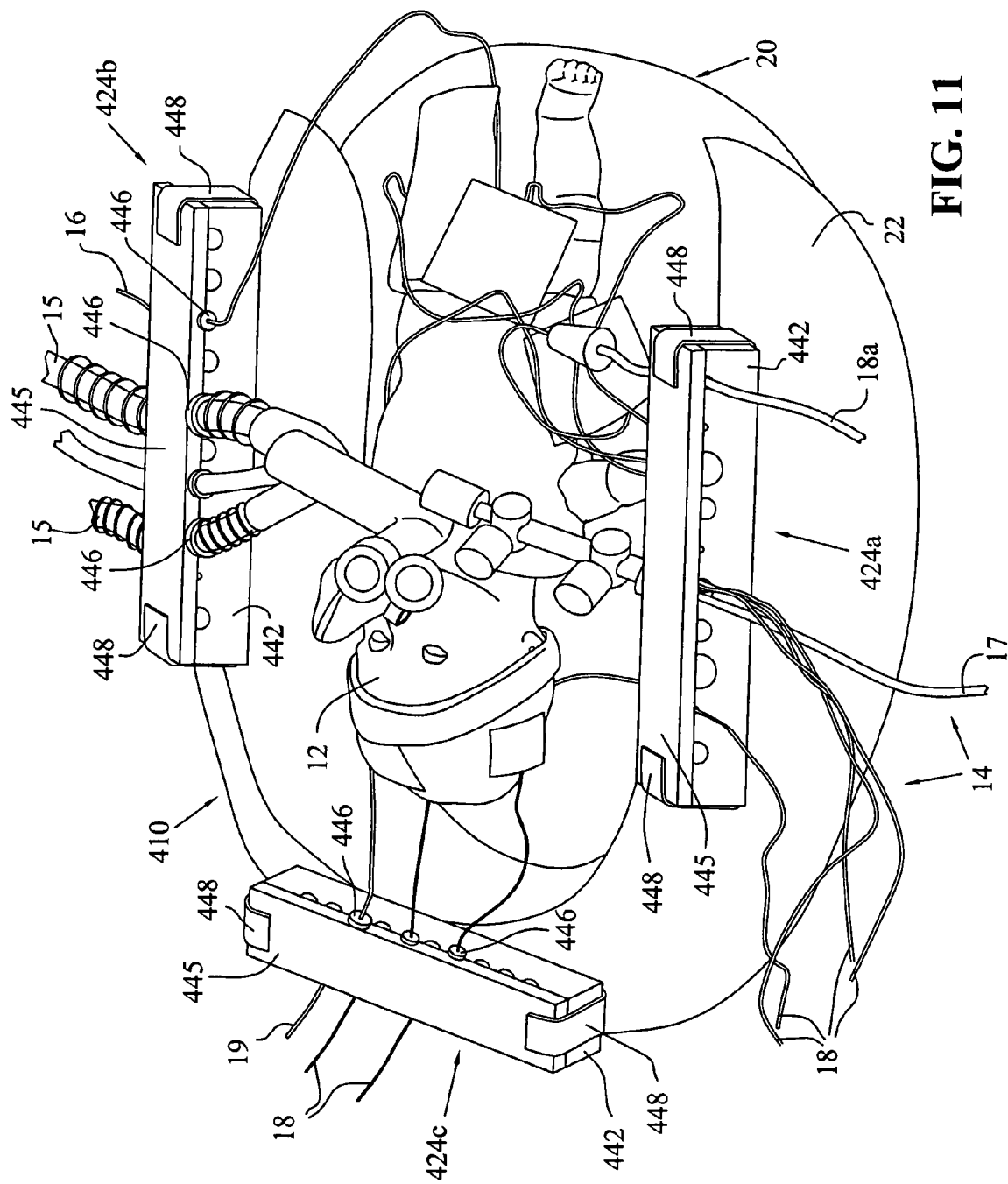
FIG. 11 is a perspective view of another embodiment of an infant transferring and holding device and lifeline securing mechanisms.
Figure 12:
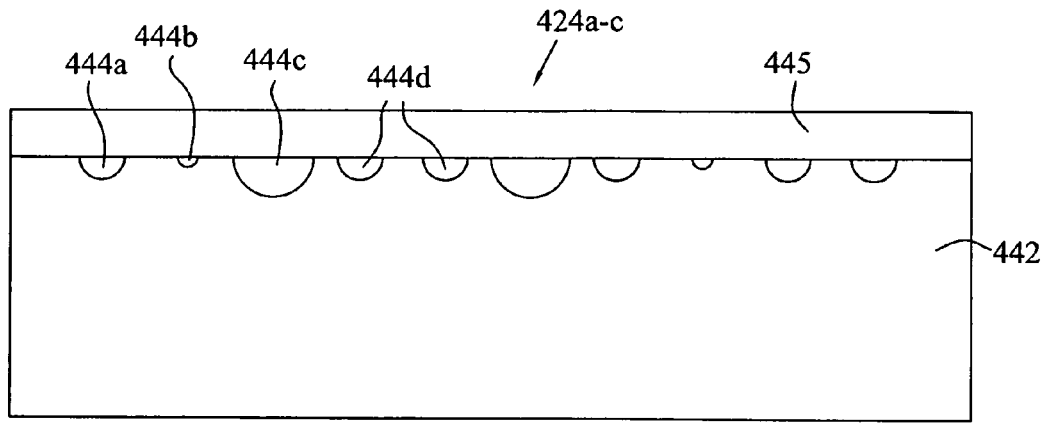
FIG. 12 is a side view of one of the lifeline securing mechanisms of FIG. 11.
Figure 13:
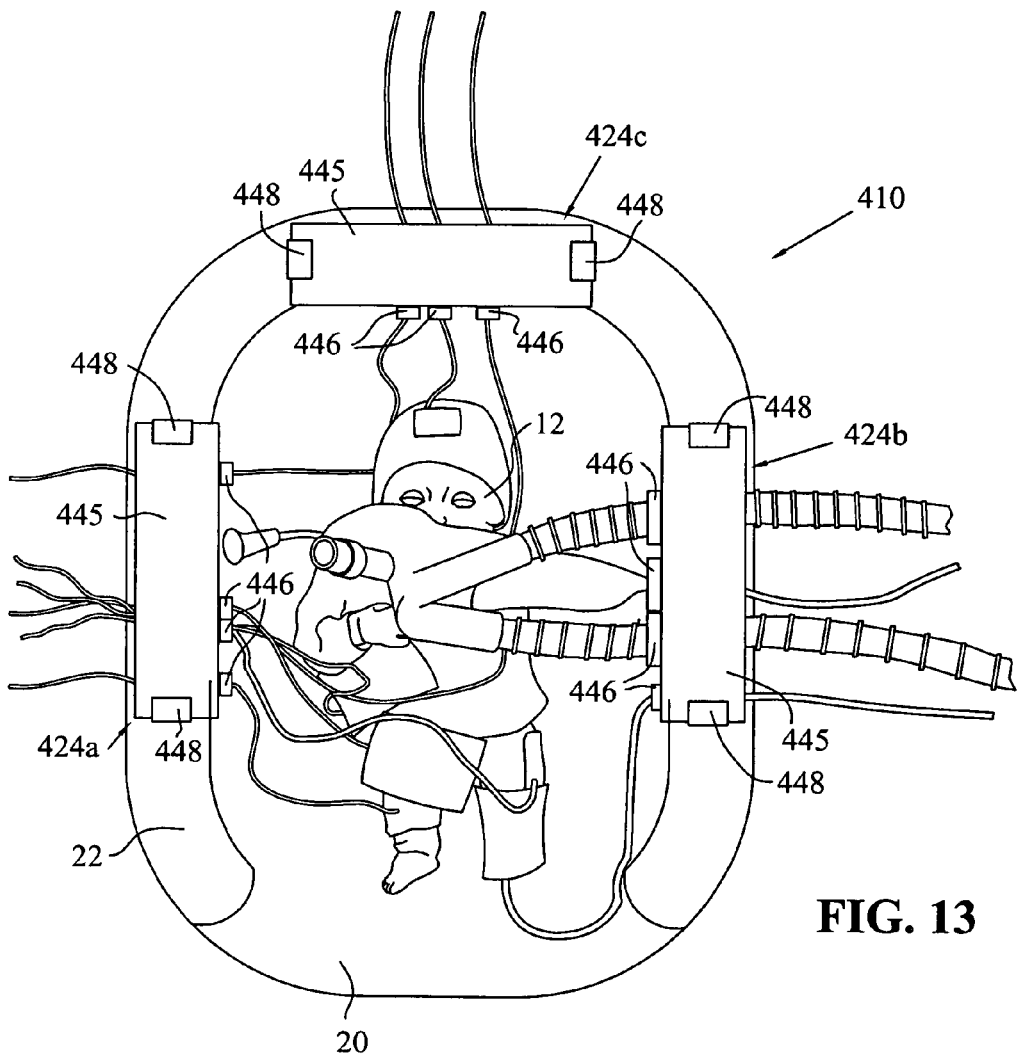
FIG. 13 is a top view of the lifeline securing mechanisms of FIG. 11.

Now referring to FIGS. 11-13, another alternate embodiment transferring and holding device is shown, generally indicated as 410. Device 410 includes support surface 20 and boundary 22 similar to device 10; however, device 410 incorporates alternate embodiment securing mechanisms, generally indicated as 424a, 424b, and 424c. Securing mechanisms 424a-424c each include a base having a multiplicity of slots, a portion of which are indicated as 444a-444d, extending transversely across the top thereof as shown in FIG. 12. In the embodiment shown, the slots 444a-444d have varied sizes to better accommodate the different sizes of lifelines 14; however, it should be appreciated that the size and shape of the slots may be varied as desired as to best accommodate lifelines 14 or the slots may be of a uniform size or shape. Securing mechanisms 424a-424c also each include a cap 445; collars 446, which are attached to and sized to respective lifelines 14; and securing devices 448.

To assemble and use transferring and holding device 410, collars 446 are attached to respective lifelines 14 using an adhesive in an area that will coincide with the inside of respective securing mechanisms 424a-424c (FIG. 11). The lifelines are placed in respective slots 444a-444d of the appropriate base 442 and caps 445 are placed over the slots and secured with securing devices 448 to secure the lifelines. The securing mechanisms are attached and located on boundary 22 using hook and loop fasteners or other known techniques. In this arrangement, the lifelines can slacken in towards infant 12, but the collars limit outward movement of the lifelines by contacting the respective securing mechanisms 424a-424c to prevent the lifelines from being disconnected from the infant.

Figure 14:
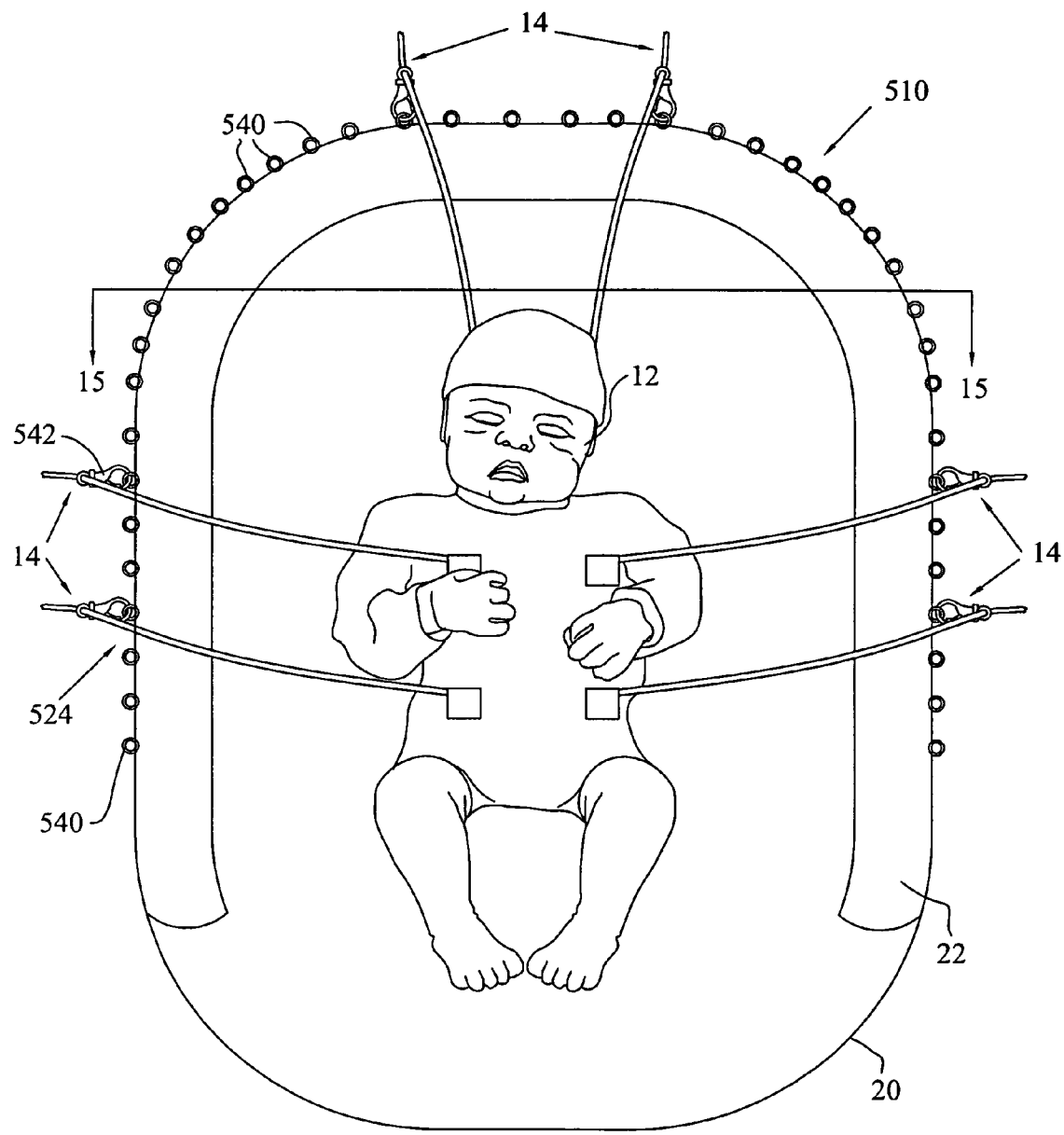
FIG. 14 is a plan view of yet another embodiment of an infant transferring and holding device and lifeline securing mechanisms.
Figure 15:
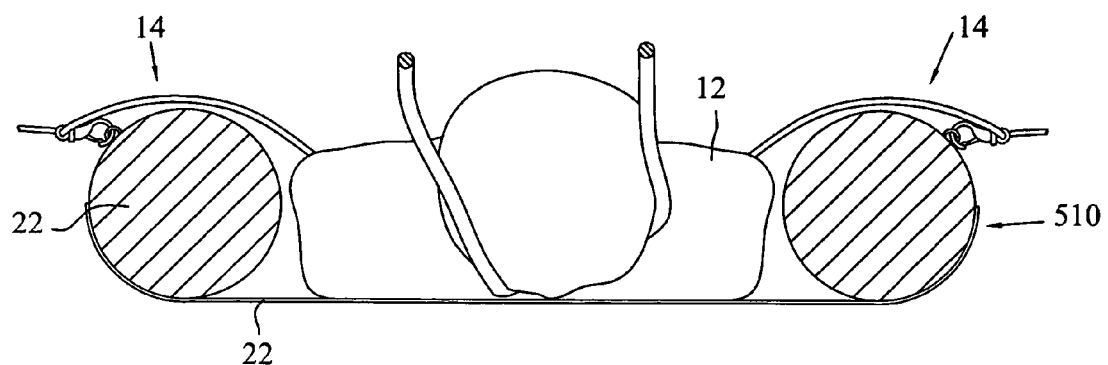
FIG. 15 is a cross-sectional view of the securing mechanisms taken along line 15-15 of FIG. 14 showing the lifelines secured to the device.
Figure 16:
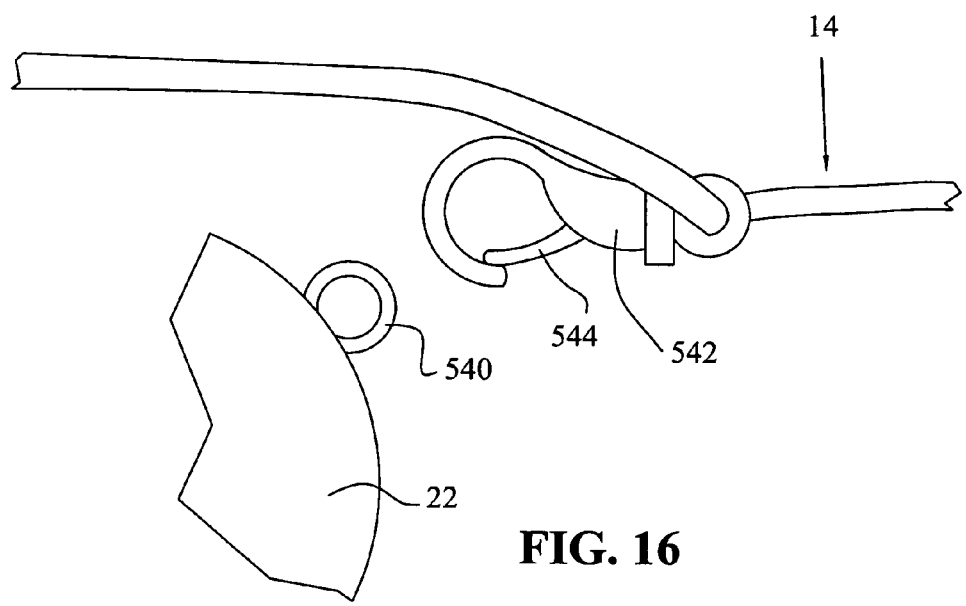
FIG. 16 is an enlarged view of a hook and a ring of the lifeline securing mechanisms of FIG. 14.

Another alternate embodiment transferring and holding device is shown, generally indicated as 510, in FIGS. 14 and 15. Device 510 includes a securing mechanism, generally indicated as 524, that has a plurality of rings 540 attached to boundary 22 and a plurality of clips or hooks 542 attached to respective lifelines 14. Clips 542 may include a releasable spring-biased clasp 544, as best shown in FIG. 16, to better secure the clips to rings 542. Alternately, the clips may be attached to the boundaries and the rings to the lifelines.

While the invention has been taught with specific reference to these embodiments, one skilled in the art will recognize that changes can be made in form and detail without departing from the spirit and scope of the invention. For example, it should be appreciated that the different support surfaces, boundaries, and securing mechanisms disclosed in the various embodiments may be interchanged, and that the number and location of securing mechanisms can be varied as desired based upon the size, type and number of lifelines attached to the infant. In addition, other techniques may be used to secure the lifelines to the securing mechanisms, such as attaching a magnet or magnetizable material to the lifelines and attaching a corresponding attractive magnet or magnetizable material to the securing mechanisms. The described embodiments are to be considered, therefore, in all respects only as illustrative and not restrictive. As such, the scope of the invention is indicated by the following claims rather than by the description.

The invention claimed is:

1. A transferring and holding device for holding infants having lifelines, including IV tubes, monitor wire leads, and ventilator tubes, connected thereto, the transferring and holding device including:
    a support surface adapted to hold an infant, said support surface defining a plane in which the infant lies and having openings to enable skin-to-skin contact between the infant and a person holding the infant;
    a flexible generally U-shaped boundary attached to and bolstering the support surface, wherein the U of U-shaped boundary lies in a plane generally parallel to the plane defined by the support surface for holding an infant; and
    at least one securing mechanism adapted to secure the lifelines and to impede the lifelines from being disconnected from the infant.

2. The transferring and holding device as set forth in claim 1, wherein at least a portion of the support surface is a non-absorbent open-weave webbed material.

3. The transferring and holding device as set forth in claim 1, wherein the boundary includes a foam member.

4. The transferring and holding device as set forth in claim 1, wherein the boundary includes a flexible plastic or metal member to provide structural support.

5. The transferring and holding device as set forth in claim 1, wherein the boundary is removable for separate washing of or replacement of the support surface.

6. The transferring and holding device as set forth in claim 5, wherein the support surface includes sleeves for insertion of at least a portion of the boundary to facilitate removable attachment thereof.

7. The transferring and holding device as set forth in claim 1, including at least two securing mechanisms, one of the securing mechanisms being located on the transferring and holding device at a base of the U-shape in an area that is above a region on the support surface configured to hold the head of the infant.

8. The transferring and holding device as set forth in claim 1, wherein the securing mechanism includes a base and spaced-apart pegs extending from the base.

9. The transferring and holding device as set forth in claim 8, wherein some of the pegs are spaced apart to receive ventilator tubes therebetween, and other pegs are configured for wrapping smaller lifelines therearound for securing the lifelines to the securing mechanism.

10. The transferring and holding device as set forth in claim 9, wherein the securing mechanism includes a cap, and the securing mechanism is configured for lifelines to be positioned between the base and the cap.

11. The transferring and holding device as set forth in claim 10, wherein the cap includes openings configured and spaced apart to receive corresponding pegs.

12. The transferring and holding device as set forth in claim 11, further including a securing device to secure the cap to the base.

13. A transferring and holding device for holding infants having lifelines, including IV tubes, monitor wire leads, and ventilator tubes, connected thereto, the transferring and holding device including:
    a support surface adapted to hold an infant, said support surface defining a plane in which the infant lies;
    a flexible generally U-shaped boundary attached to and bolstering the support surface, wherein the U of U-shaped boundary lies in a plane generally parallel to the plane defined by the support surface for holding an infant;
    at least one securing mechanism adapted to secure the lifelines and to impede the lifelines from being disconnected from the infant, and wherein the securing mechanism has a base having slots for receipt of the lifelines and collars that are attachable to and movable with the lifelines to limit the movement of the lifelines with respect to the boundary by contacting said base as the lifelines move in a direction away from the infant.

14. The transferring and holding device as set forth in claim 13, further including a cap covering the slots in the base of a securing mechanism.

15. The transferring and holding device as set forth in claim 1, wherein the securing mechanism includes hooks and rings.

16. The transferring and holding device as set forth in claim 15, wherein one of the hooks or rings are attachable to respective lifeline and the other are attached to the boundary.

17. The transferring and holding device as set forth in claim 16, wherein the hooks include a releasable clasp.

18. A transferring and holding device for holding infants having lifelines, including IV tubes, monitor wire leads, and ventilator tubes, connected thereto, the transferring and holding device including:
    a support surface adapted to hold an infant, and wherein the support surface includes openings to enable skin-to-skin contact between the infant and a person holding the infant; and
    at least one securing mechanism adapted to secure the lifelines and to impede the lifelines from being disconnected from the infant, at least a portion of the securing mechanism being attached to the transferring and holding device and located in an area that extends above a region on the support surface configured to hold the head of the infant and located substantially in line with an axis of the infant through the infant's torso, neck and head as the infant is lying on the support surface.

19. The transferring and holding device as set forth in claim 18, wherein the securing mechanism is relocatable on the transferring and holding device.

20. The transferring and holding device as set forth in claim 18, further including a boundary attached to and bolstering the support surface.

21. The transferring and holding device as set forth in claim 20, wherein the boundary has a generally U-shaped configuration with the base of the U extending above the region of the support surface configured to hold the head of the infant, and the U-shape lies in a plane substantially parallel to a plane defined by the support surface.

22. The transferring and holding device as set forth in claim 20, wherein the boundary includes a foam member.

23. The transferring and holding device as set forth in claim 20, wherein the boundary includes a plastic or metallic member that adds structural support to the device.

24. The transferring and holding device as set forth in claim 18, wherein the securing mechanism includes a base and pegs extending from and spaced apart on the base, and wherein some of the pegs are spaced to receive ventilator tubes therebetween, and others are configured for wrapping smaller lifelines therearound to limit movement of the lifelines relative to the securing mechanism.

25. A transferring and holding device for holding infants having lifelines, including IV tubes, monitor wire leads, and ventilator tubes, connected thereto, the transferring and holding device including:
    a support surface adapted to hold an infant; and
    at least one securing mechanism adapted to secure the lifelines and to impede the lifelines from being disconnected from the infant, at least a portion of the securing mechanism being attached to the transferring and holding device and located in an area that extends above a region on the support surface configured to hold the head of the infant and located substantially in line with an axis of the infant through the infant's torso, neck and head as the infant is lying on the support surface, and wherein the securing mechanism has a base having slots configured to receive lifelines and collars that are attachable to and movable with the lifelines to limit movement of the lifelines with respect to an infant on the transferring and holding device.

26. The transferring and holding device as set forth in claim 18, wherein the securing mechanism includes hooks and rings, and one of either the hooks or rings are attachable to respective lifelines and the other are attached to the transferring and holding device.

27. A method for transferring and holding an infant having lifelines, including IV tubes, monitor wire leads, and ventilator tubes, connected between the infant and medical equipment so as to impede the lifelines from being disconnected from the infant when transferring the infant from a bed into the arms of a person holding the infant, the method including the steps of:
   providing a transferring and holding device including a support surface configured to hold an infant and at least one securing mechanism to secure lifelines connected to the infant;
   providing openings in the support surface to enable skin-to-skin contact between the infant and the person holding the infant;
   placing the infant on the support surface;
   securing the lifelines to the securing mechanism before moving the infant; and
   transferring the infant from a bed into the arms of a person to hold the infant using the transferring and holding device.

28. The method for transferring and holding an infant having lifelines as set forth in claim 27, including the step of providing a boundary on the transferring and holding device that bolsters the support surface.

29. The method for transferring and holding an infant having lifelines as set forth in claim 28, wherein the boundary has a generally U-shaped configuration with the bottom of the U extending over the infant's head, and the U-shape lies in a plane substantially parallel to a plane defined by the support surface.

30. The method for transferring and holding an infant having lifelines as set forth in claim 28, wherein the boundary includes a flexible plastic or metallic member to provide structural support to the transferring and holding device and securing mechanism.

31. The method for transferring and holding an infant having lifelines as set forth in claim 27, wherein at least a portion of the securing mechanism is located over the top of the head of the infant, and is further located substantially in line with an axis of the infant through the infant's torso, neck and head as the infant is lying on the support surface.

32. The method for transferring and holding an infant having lifelines as set forth in claim 27, wherein the securing mechanism includes a base and pegs that are spaced apart on and extending from the base.

33. The method for transferring and holding an infant having lifelines as set forth in claim 32, further including the step of wrapping at least one of the lifelines around the pegs to secure the lifeline thereto.

34. The method for transferring and holding an infant having lifelines as set forth in claim 27, wherein the securing mechanism has a base having slots configured to receive lifelines and collars that are attachable to and movable with the lifelines.

35. The method for transferring and holding an infant having lifelines as set forth in claim 34, further including the step of attaching collars to respective lifelines to limit the movement of the lifelines relative to the securing mechanism by said collars contacting said base of said securing mechanism as the lifelines move in a direction away from the infant.

36. The method for transferring and holding an infant having lifelines as set forth in claim 27, wherein the securing mechanism includes hooks and rings.

37. The method for transferring and holding an infant having lifelines as set forth in claim 36, further including the steps of attaching one of either the hooks or rings to the transferring and holding device and the other to respective lifelines and securing the hooks to respective rings to limit movement of the lifelines with respect to the transferring and holding device.

* * * * *